(12) United States Patent
Pond et al.

(10) Patent No.: US 8,999,297 B2
(45) Date of Patent: Apr. 7, 2015

(54) HEMOSTATIC AGENT

(75) Inventors: Gary J. Pond, Racine, WI (US); John Baeten, San Diego, CA (US)

(73) Assignee: Inter-Med, Inc., Racine, WI (US)

( * ) Notice: Subject to any disclaimer, the term of this patent is extended or adjusted under 35 U.S.C. 154(b) by 349 days.

(21) Appl. No.: 12/460,044

(22) Filed: Jul. 13, 2009

(65) Prior Publication Data
US 2010/0136141 A1 Jun. 3, 2010

Related U.S. Application Data

(60) Provisional application No. 61/134,617, filed on Jul. 11, 2008.

(51) Int. Cl.
*A61K 33/14* (2006.01)
*A61K 31/19* (2006.01)
*A61K 33/06* (2006.01)

(52) U.S. Cl.
CPC ............. *A61K 33/14* (2013.01); *A61K 31/19* (2013.01); *A61K 33/06* (2013.01)

(58) Field of Classification Search
USPC ................ 424/78.02, 484, 677, 681, 722
See application file for complete search history.

(56) References Cited

U.S. PATENT DOCUMENTS

| 4,042,685 | A | * | 8/1977 | Smith | 424/689 |
| 6,475,470 | B1 | * | 11/2002 | Kayane et al. | 424/49 |
| 7,303,759 | B2 | * | 12/2007 | Mershon | 424/443 |
| 8,475,773 | B2 | * | 7/2013 | Giles | 424/49 |
| 2005/0244344 | A1 | * | 11/2005 | Giles | 424/49 |
| 2006/0013857 | A1 | * | 1/2006 | Kronenthal | 424/426 |
| 2008/0199539 | A1 | * | 8/2008 | Baker et al. | 424/684 |

OTHER PUBLICATIONS

"Hemostatic", The Free Dictionary [online], 2004-2009, [retrieved May 13, 2014], Retrieved from the Internet: <URL: http://medical-dictionary.thefreedictionary.com/hemostatic>.*

* cited by examiner

*Primary Examiner* — Jane C Oswecki
(74) *Attorney, Agent, or Firm* — Quarles & Brady LLP

(57) ABSTRACT

A generally non-acidic hemostatic agent, having a relatively neutral pH comprising a magnesium compound, such as a magnesium chloride, a magnesium sulfate and/or a magnesium acetate based compound. The resultant agent is generally less caustic than previous agents, when using a similar amount of active material.

20 Claims, No Drawings

HEMOSTATIC AGENT

RELATED APPLICATION

This application claims the benefit of provisional patent application Ser. No. 61/134,617, filed 11 Jul. 2008.

BACKGROUND OF THE INVENTION

The present invention is in the field of hemostatic and acid etch compositions or agents, more particularly hemostatic compositions and agents for use in providing hemostasis in oral tissues and etching compositions used in etching teeth.

In the course of performing certain dental procedures it is often desirable to use a hemostatic agent in order to stop the bleeding of oral tissues. For example, during dental reconstruction or preparation of dental crowns it is common for dentists to cut gingival or gum tissue in order to fully expose the tooth prior to taking an impression of the tooth. In order to make an accurate impression of the tooth it is advantageous for it to be clean and dry. For this reason, a hemostatic agent may be used to reduce or eliminate bleeding so that a more accurate impression of the patient's tooth can be taken.

In the case of invasive dental procedures, such as preparing the tooth to receive a crown or a root canal, enamel and dentin may be removed to expose the pulp chamber. A hemostatic agent helps stop or slow bleeding of the exposed pulp. Hemostatic agents of various types have been used successfully to stop or slow the bleeding of oral tissues during a variety of dental or oral procedures. However, prior art hemostatic agents tend to be quite acidic (i.e., typically having a pH of about 1-2), with a main component of the agent or composition being an alumina compound, such as aluminum chloride. Such agents are generally unpleasant tasting for the patient and care must be taken to limit the amount of excess material the patient may swallow.

SUMMARY OF THE INVENTION

The present invention provides a generally non-acidic hemostatic agent, having a relatively neutral pH. The agent generally comprises a magnesium compound, such as a magnesium chloride, a magnesium sulfate, and/or a magnesium acetate based compound. The resultant agent is generally less caustic than previous agents, when using a similar amount of active material. The agent is designed to perform at least as well as prior art agents, and preferably less irritable for the patient during a procedure.

It is another object of the present invention to provide a hemostatic agent that is clear in color, which minimizing any staining of teeth or gums associated with prior art agents.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

A hemostatic agent, comprising at least one magnesium based compound, is disclosed. A preferred magnesium compound is $MgCl_2.(6H_2O)$, magnesium chloride hexahydrate. The hemostatic agent further can comprise a second magnesium compound, such as $MgSO_4.(7H_2O)$ magnesium sulfate, commonly referred to as bitter salt and/or Epsom Salt. The anhydrous forms of these magnesium compounds could be used, as well. The magnesium compound or compounds of the hemostatic agent generally comprise up to about 1.0-90.0% of the overall agent, with a preferred amount being between about 40%-60% of the overall composition. The amount of magnesium material within the agent can be varied, based upon the desired viscosity of the hemostatic agent.

The hemostatic agent also comprises an acidic compound. Preferred examples include dicarboxylic acids, salts of the dicarboxylic acids, and derivatives thereof. Malonic acid, $CH_2(COOH)_2$, also referred to as propanedioic acid, is an example of a preferred dicarboxylic acid, with the ionized form of malonic acid, as well as its salts, known as malonates, also being acceptable compounds. Another preferred dicarboxylic acid is oxalic acid, $H_2C_2O_4$ or $HO_2CCO_2H$. These acids provide the necessary etching qualities for the hemostatic agent. Acids generally comprise about 0.1-20.0% of the overall hemostatic composition.

The hemostatic agent according to the present invention generally comprises an aqueous carrier. Preferably deionized water is used in the agent, comprising about 1%-60% of the agent, and more preferably between 10%-30% of the agent. The carrier also can include a polyol. Examples of suitable polyols include polyethylene glycol, glycerin, propylene glycol, dipropylene glycol, polypropylene glycol, sorbitol, and the like. Polyols used can have a wide variety of molecular weights, with higher molecular weight polyols generally increasing the viscosity of the acidic compositions according to the invention. For example, polyols having an average molecular weight (number average) of at least about 600 atomic mass units (a.m.u.) may be included in order to control the viscosity of the resulting composition. It should be understood that polyols having an average molecular weight of up to 100,000 a.m.u. or more may also be used. In some cases it may be desirable to mix two or more different polyols together having different molecular weights in order to yield a composition having the desired properties. When a polyol is included within the composition according to the invention, they are preferably included in an amount in a range from about 0.1% to about 50% by weight of the composition, and more preferably in a range of about 5% to about 40% by weight. An example of one such polyol is Poly EO 400, or polyethylene oxide 400, comprising about 5%-25% of the hemostatic agent.

Hemostatic agents can have a displeasing taste for the patient, especially the acidic compounds that comprise the hemostatic agents. As such, it is contemplated to include at least one sweetening compound that can be used to mask or disguise the bitterness associated with the etching compounds of the hemostatic agent. An example of such a compound is xylitol is a five-carbon sugar alcohol that is used as a sugar substitute. Preferably, sugar substitutes are used, as they limit residual effects, such as tooth decay, and have a moisturizing and emollient effect during the application process.

The present invention intends to provide a hemostatic agent that is not as acidic as previous agents. Prior art hemostatic agents are quite acidic, having a pH of about 1.0-2.0. The present invention provides a hemostatic agent having a more neutral composition, with a preferred pH of from about 3.0 to up to about 8.0, with a more preferred pH from about 6.0-8.0. To achieve this, preferably a weak base is added to the composition to balance the pH of the solution. Possible compounds include amines and similar compounds. One such example is triethanolamine, often abbreviated as TEA. Potassium hydroxide and sodium hydroxide are also possible compounds. Depending on the amount of acids and hemostatic compound present in the agent, the pH balancing agent could comprise up to about 20% of the overall composition of the hemostatic agent.

A thickening agent may also be added to the hemostatic agent to provide the necessary consistency and viscosity for the hemostatic agent. The polyols, discussed above, can act as thickening agents, especially polyols having higher molecular weights. Other thickening agents include xanthan gum (Food Grade) and similar materials, which also act to assist in stabilizing the pH for the composition. Xantham gums sold under the brand name Keltrol®, sold by the CP Keltrol Company, are suitable compounds, which can comprise up to about 25% of the overall weight, and preferably up to about 5% of the overall weight.

A hemostatic agent was prepared according to the present invention, by the following steps:

1. Deionized water is charged into a stainless steel vessel and agitated.

2. With agitation continuing, $MgCl_2 \cdot (6H_2O)$ is added to the vessel.

3. $MgSO_4 \cdot (7H_2O)$ is added to the vessel, with continuous agitation. Agitation should continue until all solids have dissolved in the deionized water.

4. The acid compounds (i.e. malonic acid and oxalic acid) are added to the solution during agitation.

5. Xylitol is added to the solution, followed by adding TEA, continuously agitating until the solution is clear.

6. Poly EO 400 is added during agitation.

7. Keltrol is added slowly to the solution in the vessel by sprinkling the Keltrol onto the mixture, still during agitation. Agitation is continued until the Keltrol is completed hydrated within the solution, forming a uniform clear gel with no suspended solids.

It is understood that other methods could be used as well to produce a hemostatic agent according to the present invention. The qualities of the resultant agent were recorded, and recited below in Table 1.

TABLE 1

| Compound | Weight Percentage (w/w %) |
| --- | --- |
| Deionized $H_2O$ | 19.60 |
| $MgCl_2 \cdot (6H_2O)$ | 31.25 |
| $MgSO_4 \cdot (7H_2O)$ | 16.75 |
| Malonic Acid | 1.00 |
| Oxalic Acid | 0.40 |
| Poly EO 400 | 12.00 |
| Xylitol | 10.00 |
| TEA | 7.00 |
| Keltrol ® T-630 | 2.00 |
| pH | ~7.44 |

As shown, the compound has a relatively neutral pH (~7.44), which provides a much more non-corrosive, gentle, and acceptable compound for the patient.

The compound was tested for various qualities, such as viscosity, color, and other similar qualities. The results in Table 1 is only an example of a possible composition for an agent according to the present invention. Table 2 provides preferable composition ranges according to the present invention.

TABLE 2

Preferred Ranges

| Compound | Weight Percentage (w/w %) |
| --- | --- |
| Deionized $H_2O$ | 10.0%-90.0% |
| $MgCl_2$ | 1.0%-50.0% |
| $MgSO_4$ | 0.5%-40.0% |
| Malonic Acid | 0.1%-10.0% |
| Oxalic Acid | 0.1%-10.0% |
| Poly EO 400 | 2.0%-50.0% |
| Xylitol | 1.0%-20.0% |
| TEA | 2.0%-15.0% |
| Keltrol ® T-630 | 0.5%-10.0% |
| pH | ~3.0-~8.0 |

Not only are the agents of the present invention are as agreeable or more agreeable as compared to the prior art by being less acidic than prior art agents, they also have a clear, translucent or transparent appearance. These agents minimize staining and discoloration of the teeth and the gums, which is an added aesthetic feature of the present invention.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An aqueous dental hemostatic agent comprising:
   at least one water-soluble magnesium salt selected from the group consisting of magnesium chloride, magnesium sulfate, magnesium acetate, magnesium citrate and combinations thereof, said at least one magnesium salt at between 40-60 weight percent of the agent;
   an acidic compound;
   a pH balancing compound between 2-15 weight percent of the agent;
   and
   KELTROL® T-630 xanthan gum at between 0.5-10.0 weight percent of the agent,
   said agent having a pH value between about 3.0-8.0.

2. The hemostatic agent according to claim 1 wherein said at least one water-soluble magnesium salt comprises a first water-soluble magnesium salt and a second water-soluble magnesium salt, and wherein said first water-soluble magnesium salt comprises magnesium chloride.

3. The hemostatic agent according to claim 2 wherein said second water-soluble magnesium salt comprises magnesium sulfate or magnesium acetate.

4. The hemostatic agent according to claim 2, wherein said first water-soluble magnesium salt comprises between about 1.0-50.0 weight percent of the hemostatic agent.

5. The hemostatic agent according to claim 3 wherein said second water-soluble magnesium salt comprises between about 0.5-40.0 weight percent of the hemostatic agent.

6. An aqueous, clear dental hemostatic agent comprising:
   a first water-soluble magnesium compound comprising between 1.0-50.0 weight percent of the agent, and a second water-soluble magnesium compound comprising between 0.5-40.0 weight percent of the agent, the first and second water-soluble magnesium compounds selected from the group consisting of magnesium chloride, magnesium sulfate, magnesium acetate, and magnesium citrate, the combination of said first and second water-soluble magnesium compounds comprising between 40.0-60.0 weight percent of the agent;

a first acidic compound; and a xanthan gum comprising between 0.5-10.0 weight percent, said agent having a pH value between about 3.0-8.0;

wherein said dental hemostatic agent is a uniform composition with no suspended solids.

7. The agent according to claim 6 further comprising a polyol.

8. The agent according to claim 6 further comprising a second acidic compound.

9. The agent according to claim 1, wherein said acidic compound is a dicarboxylic acid compound.

10. The agent according to claim 9, wherein said dicarboxylic acid compound is selected from malonic acid and oxalic acid.

11. The agent according to claim 1, wherein the pH balancing compound comprises triethanolamine at between 2.0-20 weight percent of the hemostatic agent.

12. The agent according to claim 6, wherein said first acidic compound is a dicarboxylic acid compound.

13. The agent according to claim 12, wherein said dicarboxylic acid compound is selected from malonic acid and oxalic acid.

14. The agent according to claim 6, further comprising triethanolamine at between 2.0-20 weight percent of the hemostatic agent.

15. The agent according to claim 6, wherein said first water-soluble magnesium compound is magnesium chloride and wherein said second water-soluble magnesium compound is magnesium sulfate.

16. A hemostatic agent obtained in a process comprising the steps of:
   (a) dissolving at least one magnesium salt in a volume of water;
   (b) combining at least one acidic compound with the mixture of step (a);
   (c) adding a pH balancing compound to the mixture of step (b) and agitating to provide a clear solution;
   (d) adding a polyol to the clear solution of step (c);
   (e) adding KELTROL® T-630 xanthan gum to the mixture of step (d);
   (f) agitating the mixture of step (e) to completely hydrate the xanthan gum, thereby forming a uniform clear gel with no suspended solids and a pH between about 3.0 and about 8.0, the uniform gel comprising:
       about 40 weight percent to about 60 weight percent of the at least one magnesium salt;
       about 0.1 weight percent to about 20 weight percent of the at least one acidic compound;
       about 1 weight percent to about 20 weight percent of a sweetener;
       up to about 20 weight percent of the pH balancing compound;
       about 5 weight percent to about 25 weight percent of the polyol; and
       about 0.5 weight percent to about 10.0 weight percent of the xanthan gum.

17. The hemostatic agent of claim 16, wherein a first water-soluble magnesium salt is magnesium chloride and wherein a second water-soluble magnesium salt is magnesium sulfate.

18. The hemostatic agent of claim 16, wherein said acidic compound is a dicarboxylic acid compound selected from malonic acid and oxalic acid.

19. The hemostatic agent of claim 16, wherein the pH balancing compound is triethanolamine.

20. The hemostatic agent of claim 16, wherein the said polyol is polyethylene oxide 400.

* * * * *